United States Patent
Patrascu et al.

(10) Patent No.: US 7,586,012 B2
(45) Date of Patent: Sep. 8, 2009

(54) PROCESS FOR RECOVERING AN ADDUCT OF A BIS(4-HYDROXYARYL)ALKANE AND A PHENOLIC COMPOUND

(75) Inventors: Emil Patrascu, Stade (DE); Johann-Wilhelm Frey, Stade (DE); Manfred Hagel, Himmelpforten (DE)

(73) Assignee: Dow Global Technologies Inc.

( * ) Notice: Subject to any disclaimer, the term of this patent is extended or adjusted under 35 U.S.C. 154(b) by 290 days.

(21) Appl. No.: 10/541,779

(22) PCT Filed: Jan. 16, 2004

(86) PCT No.: PCT/US2004/001118
§ 371 (c)(1),
(2), (4) Date: Jan. 6, 2006

(87) PCT Pub. No.: WO2004/076394
PCT Pub. Date: Sep. 10, 2004

(65) Prior Publication Data
US 2006/0224025 A1    Oct. 5, 2006

(51) Int. Cl.
*C07C 37/68* (2006.01)
*C07C 39/12* (2006.01)

(52) U.S. Cl. .................. 568/724; 568/722; 568/729

(58) Field of Classification Search .................. None
See application file for complete search history.

(56) References Cited
FOREIGN PATENT DOCUMENTS
DE        19961521 A1 *  6/2001

\* cited by examiner

*Primary Examiner*—Karl J Puttlitz

(57) ABSTRACT

A process for recovering a solid adduct of a bis(4-hydroxyaryl)alkane and a phenolic compound from a suspension comprising the addict is disclosed. The process comprises the steps of a) supplying the suspension to a rotary filter, b) filtering the supplied suspension in the rotary filter to retain adduct as an adduct cake, c) pre-drying the adduct cake with an inert gas, d) washing the pre-dried adduct cake, e) optionally drying the washed adduct cake, and f) discharging the washed adduct cake from the rotary filter.

20 Claims, 1 Drawing Sheet

Figure 1:
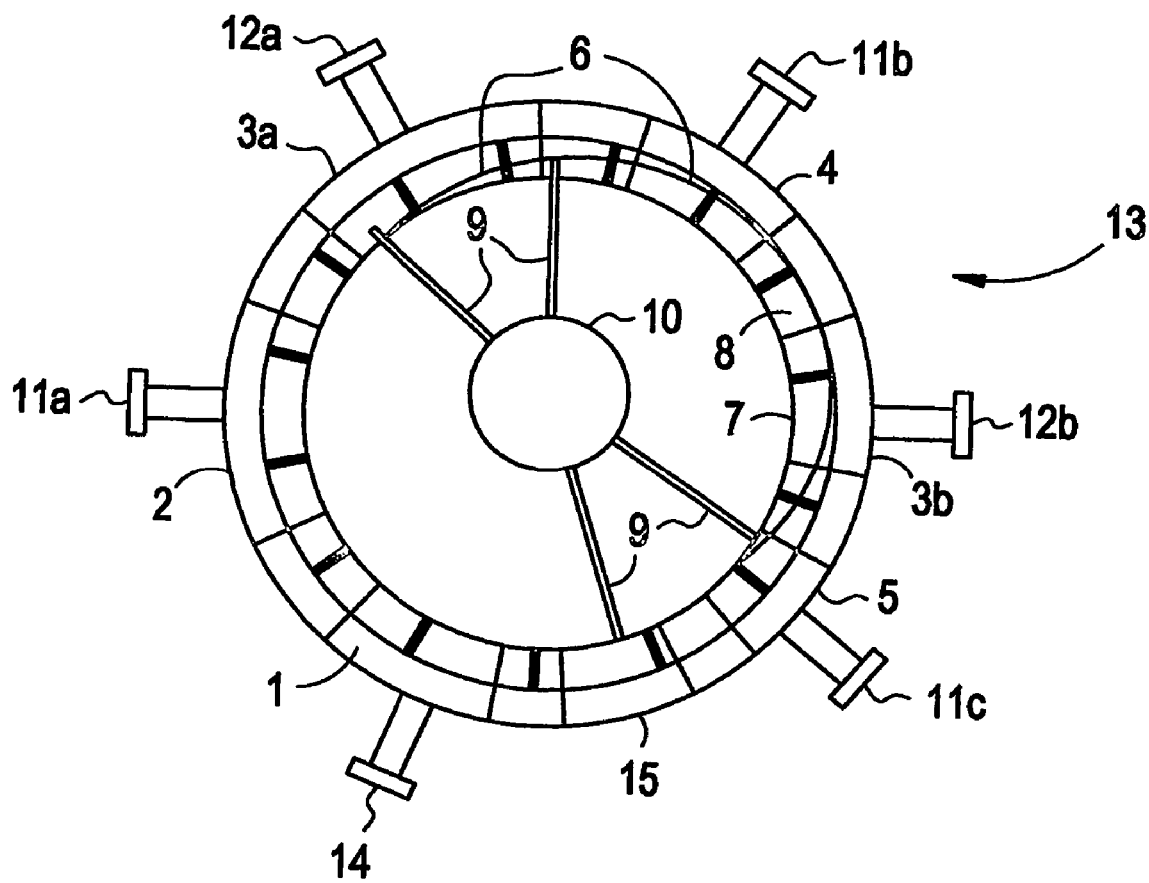

PROCESS FOR RECOVERING AN ADDUCT OF A BIS(4-HYDROXYARYL)ALKANE AND A PHENOLIC COMPOUND

The present invention relates to a process for recovering a solid adduct of a bis(4-hydroxyaryl)alkane and a phenolic compound from a suspension comprising the adduct, to a process for recovering a bis(4-hydroxyaryl)alkane as well as to the solid adduct and a bis(4-hydroxyaryl)alkane producible according to these processes.

BACKGROUND OF THE INVENTION

Bis(4-hydroxyaryl)alkanes, which are the condensation products of a phenol compound with a carbonyl compound in the presence of an acid catalyst, are used in the manufacturing of many commercial products, such as polycarbonates and epoxy resins. Of particular technical and commercial importance is the condensation product of phenol and acetone, 2,2-bis(4-hydroxyphenyl)-propane, often called bisphenol-A. The world production of bisphenol-A in 1999 was over 2 million metric tons per year and is still growing. A very high purity of bisphenol-A is essential for the quality of the commercial products to which it is processed, such as polycarbonates. Well-known procedures for producing bisphenol-A include the steps of i) reacting an excess of phenol with acetone in the presence of an acidic catalyst to produce a product mixture containing bisphenol A; ii) passing the product mixture to a crystallizer to produce a suspension comprising a crystalline adduct of Bisphenol A and phenol, iii) separating the adduct from the mother liquor and washing the adduct crystals, and iv) distilling off the phenol from the bisphenol A:phenol adduct to obtain bisphenol A. The reaction mixture typically contains bisphenol A, non-reacted phenol, water, usually also some non-reacted acetone, but also some by-products, such as 2-(2-hydroxyphenyl)-2-(4-hydroxyphenyl)propane (o,p-isomer), 2,2,4-trimethyl-4-(4-hydroxyphenyl)chroman, polyphenols with three or more phenyl rings in the molecule, substituted indenes, hydroxyphenyl-chromanes, hydroxyphenyl-indanoles, or substituted xanthenes. These by-products cause an undesirable color to the bisphenol A:phenol adduct unless they are effectively separated from the crystalline bisphenol A:phenol adduct.

Accordingly, the skilled artisans have spent much efforts on the crystallization of bisphenol A:phenol adduct, the separation of the crystals from the mother liquor and on the purification of the bisphenol A:phenol adduct.

Numerous patent applications have been filed on the crystallization step, for example U.S. Pat. Nos. 4,740,635; 4,861,919; 4,927,973; 5,345,000 and 5,545,764. Crystallization in the presence of water, multistage crystallization and in-process crystallization are described in these publications.

WO 01/46105 A1 addresses the problem of separating the adduct crystals from the mother liquor. It suggests a process wherein the adduct crystals are separated from the mother liquor by means of continuous filtration in a rotating vacuum drum containing several filter cells and are subsequently washed with phenol and drawn off from the washing liquor by suction.

Other publications mainly relate to the washing of the adduct crystals. U.S. Pat. No. 5,434,316 discloses that the crystals are washed with hot water.

In view of the large amount of bis(4-hydroxyaryl)alkanes used in commercial production and the high requirements for their purity, it is still desirable to find a new process for recovering adducts of a bis(4-hydroxyaryl)alkane and a phenolic compound and for recovering bis(4-hydroxyaryl)alkanes. It is particularly desirable to find a new process wherein the mentioned adducts and bis(4-hydroxyaryl)alkanes of very high purity can be recovered.

SUMMARY OF THE INVENTION

One aspect of the present invention is a process for recovering a solid adduct of a bis(4-hydroxyaryl)alkane and a phenolic compound from a suspension comprising the adduct, wherein the process comprises the steps of
 a) supplying the suspension to a rotary filter,
 b) filtering the supplied suspension in the rotary filter to retain adduct as an adduct cake,
 c) pre-drying the adduct cake with an inert gas,
 d) washing the pre-dried adduct cake,
 e) optionally drying the washed adduct cake, and
 f) discharging the washed adduct cake from the rotary filter.

Another aspect of the present invention is an adduct of a bis(4-hydroxyaryl)alkane and a phenolic compound which is producible according to above-mentioned process.

Yet another aspect of the invention is a process for recovering a bis(4-hydroxyaryl)alkane wherein the adduct recovered according to the above-mentioned process is melted and the phenolic compound is distilled off.

Yet another aspect of the invention is a bis(4-hydroxyaryl)alkane obtainable according to the above-mentioned process.

SHORT DESCRIPTION OF THE DRAWING

The FIGURE illustrates a cross-sectional view on a rotary pressure filter which is useful in the process of the present invention.

DETAILED DESCRIPTION OF THE INVENTION

Slurries comprising a solid adduct of a bis(4-hydroxyaryl)alkane and a phenolic compound can be obtained by reaction of a stoichiometric excess of a phenolic compound with a carbonyl compound in the presence of an acidic catalyst.

Useful phenolic compounds are listed in U.S. Pat. No. 5,723,688, column 4, lines 7-39. Preferred examples of the compounds of formula (I) are phenol, cresols, xylenols, such as 2,6-dimethylphenol or 3,5-dimethylphenol, chlorophenols, dichlorophenols, 2-isopropyl-5-methyl-phenol, 5-isopropyl-2-methyl-phenol, 2-methyl-6-ethylphenol, 2,4-dimethyl-3-ethylphenol, 4-ethylphenol, 2-ethyl-4-methylphenol, 2,3,6-trimethylphenol, 2-methyl-4-tertiary-butylphenol, 2,4-ditertiary-butyl-phenol, 4-methyl-2-tertiary-butylphenol, 2-tertiary-butyl-4-methylphenol, 2,3,5,6-tetramethylphenols, 2,6-ditertiary-butylphenol, 3,5-diethylphenol, 2-methyl-3,5-diethylphenol, o-phenylphenol or p-phenylphenol.

Useful carbonyl compounds are ketones and aldehydes which are listed in U.S. Pat. No. 5,723,688, column 4, lines 40-67 and column 5, lines 1-4. Examples of suitable ketones include, for example, acetone, methyl ethyl ketone, diethyl ketone, dibutyl ketone, methyl isobutyl ketone and methyl amyl ketone. Examples of suitable aldehydes include formaldehyde, acetaldehyde, propionaldehyde and butyraldehyde.

The process of the present invention is particularly suitable for recovering an adduct of bisphenol A with phenol. Bisphenol A is the reaction product of acetone and phenol. However, the process of the present invention is not limited thereto.

Preferably a suspension comprising a solid adduct of a bis(4-hydroxyaryl)alkane and a phenolic compound is obtained by reaction of a stoichiometric excess of a phenolic compound with a carbonyl compound in the presence of an acidic cation exchange resin as a catalyst and treating the resulting product mixture in a crystallization device. More preferably the product mixture is not subjected to a distillation step before the product mixture is passed to the crystallization device. Such a process is described in U.S. Pat. No. 5,723,688. Prior to crystallization the resulting product mixture contains bis(4-hydroxyaryl)alkane, the non-reacted phenolic compound, some non-reacted carbonyl compound, water and by-products. The molar excess of the phenolic compound in the reaction is preferably chosen such that the product mixture comprises from 10 to 27 percent of the phenolic compound, based on the total weight of the product mixture. Prior to the crystallization step the content of the carbonyl compound, such as acetone, in the product mixture is preferably controlled and, if necessary, carbonyl compound is added such that the total concentration of the carbonyl compound is from 0.1 to 8 percent, based on the total weight of the product mixture. The weight of the water in the product mixture is preferably from 1 to 10 percent, based on the total weight of the product mixture. The product mixture is passed to a crystallization device to produce adduct crystals of the bis(4-hydroxyaryl)alkane and the phenolic compound. The crystallization of the adduct can for example be effected by cooling the product mixture in the crystallization device to a temperature from 25° C. to 75° C., more preferably from 30° C. to 65° C., most preferably from 34° C. to 58° C. The cooling of the product mixture can be effected by external cooling, for example, by means of a heat exchanger, such as a jacketed crystallization device equipped with water cooling, or by reducing the pressure in the crystallization device and evaporating water, carbonyl compound and a small amount of phenolic compound. The residence time of the product mixture in the crystallization device preferably is from 0.1 to 20 hours, more preferably from 1 to 6 hours. The major portion of the bis(4-hydroxyaryl)alkane crystallizes out as an adduct with the phenolic compound in a 1:1 molar ratio. Thereby a suspension of the adduct in a liquid, that means mother liquor, is obtained whereby the mother liquor comprises mainly the phenolic compound, some bis(4-hydroxyaryl)alkane, by-products and optionally residual amounts of non-reacted carbonyl compound and water.

Alternatively, a suspension comprising a solid adduct of a bis(4-hydroxyaryl)alkane and a phenolic compound can be obtained by treatment of the mother liquor which is recovered from the above-mentioned crystallization device after separation of solid adduct of the bis(4-hydroxyaryl)alkane and the phenolic compound. The suspension can for example be obtained by cooling, concentration or another suitable treatment of the mother liquor.

Alternatively, a suspension comprising a solid adduct of a bis(4-hydroxyaryl)alkane and a phenolic compound can be obtained by slurrying a crude solid adduct of a bis(4-hydroxyaryl)alkane and a phenolic compound in a suitable liquid, such as a mixture of phenolic compound, water and acetone; or a mixture of phenolic compound and acetone; or a phenolic compound alone. Phenol is the most preferred phenolic compound.

The suspension preferably comprises from 2 to 40, more preferably from 5 to 38, most preferably from 10 to 30 weight percent of adduct crystals, from 0.5 to 8.5, more preferably from 0.8 to 6.5, most preferably from 1.2 to 4.8 weight percent of an o,p-isomer of the bisphenol compound and from 0.5 to 10.6, more preferably from 0.8 to 7.8, most preferably from 1.1 to 6.4 weight percent of other by-products, based on the total weight of the suspension. The remaining portion of the suspension typically mainly consists of the phenolic compound and optionally minor amounts of acetone and water. The amount of acetone, if present, is generally from 0.1 to 8 percent, based on the total weight of the suspension. The weight of water, if present, is generally from 1 to 10 percent, based on the total weight of the suspension.

The solid, typically crystalline, adduct of the bis(4-hydroxyaryl)alkane and the phenolic compound is recovered from the suspension in the subsequently described process which comprises the steps of a) supplying the suspension to a rotary filter, b) filtering the supplied suspension in the rotary filter to retain adduct as an adduct cake, c) pre-drying the adduct cake with an inert gas, d) washing the pre-dried adduct cake, e) optionally drying the washed adduct cake, and f) discharging the washed adduct cake from the rotary filter.

The rotary filter used in the process of the present invention can be a vacuum or pressure filter. It has been found that the use of a rotary pressure filter is preferred. Rotary pressure filters as such are generally known in the art. The pressure filter should generally be phenol-tight and gas-tight. The possibility of achieving in a rotary pressure filter a higher pressure difference between the inside and outside of the filter medium than in a rotary vacuum filter has been found to have a favorable impact on the purity of the adduct cake. Particularly preferred is a rotary pressure filter which allows continuous operation, most preferably a rotary pressure filter delivered by BHS Sonthofen which is adapted to the process of the present invention.

The FIGURE illustrates a cross-sectional view on a preferred rotary filter, more preferably a rotary pressure filter, which is useful in the process of the present invention. The following description of the invention refers to the FIGURE, however the process of the present invention is not limited thereto. The rotary filter comprises a rotary drum 13 comprising a suspension feed zone 1, a pre-drying zone 2, a first wash zone 3a, an intermediate drying zone 4, a second wash zone 3b, a drying zone 5, and a discharge zone 15. The rotary filter comprises several filtration cells 6. Each filtration cell 6 contains a filter cloth 7 in which adduct cake 8 is formed. Mother liquor is removable from each filtration cell 6 via a conduit 9 to a control head 10 which typically serves as a mother liquor outlet. The rotary filter also comprises gas feed nozzles 11a, 11b and 11c, liquid feed nozzles 12a and 12b, and a suspension feed conduit 14. Due to the internal divisions of the rotary drum 13, the adduct cake can be further processed in separate zones. It is to be understood that a rotary filter generally comprises additional parts which are not shown in the FIGURE, such as a housing and a support for the rotary drum and various additional conduits for feeding and removing materials to and from the rotary drum.

In step a) of the process of the present invention the suspension comprising the above-described adduct is supplied to the suspension feed zone 1 of the rotary filter via a suspension feed conduit 14. The suspension preferably has a pressure of from 0.1 to 5.0 bar (10 to 500 kPa), more preferably from 0.4 to 3.2 bar (40 to 320 kPa), most preferably from 0.6 to 2.4 bar (60 to 240 kPa) above atmospheric. The suspension is preferably fed into the rotary filter by means of static descending force if there is a sufficient difference in static height between the above-mentioned crystallization device and the rotary filter. To preserve the crystalline shape of the adduct of the bis(4-hydroxyaryl)alkane and the phenolic compound to the greatest possible extent, providing the pressure of the suspension by means of static height difference is preferred over the usage of a pump.

The filtration step b) is preferably conducted under an inert gas atmosphere, more preferably nitrogen. The rotary filter generally has a temperature of from 32 to 98° C., preferably from 35° C. to 85° C.; more preferably from 42° C. to 68° C. The solid adduct of a bis(4-hydroxyaryl)alkane and a phenolic compound is retained as an adduct cake 8 in the filtration cells 6. Mother liquor is passed from each filtration cell 6 via a conduit 9 to a control head 10 which typically serves as a mother liquor outlet. For the sake of simplifying the drawing only four conduits 9 are shown. By rotation of the control head 10 the filtration cells 6 filled with adduct cake 8 can pass from the suspension feed zone 1 to the pre-drying zone 2.

In step c) of the process of the present invention the adduct cake is pre-dried with an inert gas. It has been surprisingly found that the pre-drying step c) of the present invention is essential for achieving a high purity and a light color of the solid adduct of a bis(4-hydroxyaryl)alkane and a phenolic compound. Particularly when recovering a bisphenol A:phenol adduct, crystals of high purity can be achieved. Nitrogen is a preferred inert gas. The pre-drying temperature is preferably from 40° C. to 85° C., more preferably from 42° C. to 68° C. The pressure of the inert gas is preferably from 0.2 to 6 bar (20 to 600 kPa), more preferably from 0.6 to 3.8 bar (60 to 380 kPa). It can be fed into the pre-drying zone 2 via a first gas feed nozzle 11a. The adduct cake is preferably dried to a residual moisture content of less than 50 weight percent, more preferably from 6 to 42 weight percent, most preferably from 12 to 30 weight percent, based on the weight of the dry adduct cake. By rotation of the control head 10 the filtration cells 6 filled with pre-dried adduct cake 8 can pass from the pre-drying zone 2 to the first wash zone 3a.

In step d) of the process of the present invention the pre-dried adduct cake is washed. Washing liquor can be fed into a wash zone 3a and/or a second wash zone 3b via a first liquid feed nozzle 12a and/or a second liquid feed nozzle 12b. Preferred washing liquors are for example phenol, acetone, water, a phenol/acetone mixture, a phenol/water mixture, a phenol/acetone/water mixture or an acetone/water mixture. Alternatively, the pre-dried adduct cake can be washed by means of steam. The cake can be washed in single or multiple stages. If it is washed in multiple stages, the cake can be washed counter-currently or preferably co-currently. The adduct cake is preferably washed in two or more stages, more preferably in two stages, with an intermediate drying step. In a preferred embodiment of the washing step d), the adduct cake is washed in a first stage with a phenol/acetone/water mixture to remove residual amounts of mother liquor from the crystals and to eliminate or reduce impurities normally present in the mother liquor. In the phenol/acetone/water mixture the concentration of the phenol is preferably from 0.8 to 98 percent, more preferably from 2.1 to 55 percent, most preferably from 5 to 40 percent; the concentration of the acetone is preferably from 0.4 to 46 percent, more preferably from 1.1 to 25 percent, most preferably from 1.5 to 10 percent, based on the total weight mixture, and the remaining amount of the mixture is water. The temperature of the phenol/acetone/water mixture to be used in the washing step d) is preferably from 20° C. to 90° C., more preferably from 32° C. to 72° C. Preferably from 0.1 to 2.6 weight parts, more preferably from 0.4 to 1.5 weight parts of phenol/acetone/water mixture are used per weight part of the solid adduct of a bis(4-hydroxyaryl)alkane and a phenolic compound, such as bisphenol A phenol adduct. Phenol/acetone/water mixture which has been used for washing the solid adduct crystals is preferably recycled. After the first washing stage the adduct cake is preferably subjected to an intermediate drying step. An inert gas such as nitrogen is preferably used for the intermediate drying step. The temperature of the inert gas preferably is from 40° C. to 85° C., more preferably from 42° C. to 68° C. The pressure of the inert gas is preferably from 0.2 to 6 bar (20 to 600 kPa), more preferably from 0.6 to 3.8 bar (60 to 380 kPa). In the intermediate drying step the adduct cake is preferably dried to a residual moisture content of less than 50 weight percent, more preferably from 4 to 36 weight percent, most preferably from 8 to 24 weight percent, based on the weight of the dry adduct cake. In the second washing stage the adduct cake is preferably washed with phenol. The temperature of washing phenol is preferably from 42° C. to 95° C. more preferably from 44° C. to 78° C. Preferably from 0.1 to 1.6 weight parts, more preferably from 0.3 to 1.2 weight parts of wash phenol are used per weight part of the solid adduct of a bis(4-hydroxyaryl)alkane and a phenolic compound, such as bisphenol A:phenol adduct. The wash phenol, which has been used for washing the solid adduct crystals, is preferably recycled to the bisphenol production process. By rotation of the control head 10 the filtration cells 6 filled with the washed adduct cake 8 can pass from the first wash zone 3a to the intermediate drying zone 4, to the second wash zone 3b and then to the drying zone 5.

After the washing step d) the crystals are optionally dried, preferably by means of an inert gas, such as nitrogen. It can be fed into the drying zone 5 via a gas feed nozzle 11c. The temperature of the inert gas preferably is from 40° C. to 85° C., more preferably from 42° C. to 68° C. The pressure of the inert gas preferably is from 0.2 to 6 bar (20 to 600 kPa), more preferably from 0.6 to 3.8 bar (60 to 380 kPa). The adduct of a bis(4-hydroxyaryl)alkane and a phenolic compound, such as bisphenol A:phenol adduct, preferably has a residual moisture content of from 2 to 46 weight percent, more preferably from 8 to 30 weight percent, based on the weight of the dry adduct. By rotation of the control head 10 the filtration cells 6 filled with the dried adduct cake 8 can pass from the drying zone 5 to the discharge zone 15.

The washed and optionally dried adduct cake can be discharged from the rotary filter in a known manner. For example, the adduct cake can be discharged from the discharge zone 15 by means of an inert gas such as nitrogen at overpressure. The discharging step f) is preferably assisted by reverse gas blowing After discharge of the adduct cake, the filter cloth 7 is preferably washed with phenol, more preferably under the same condition as described in the washing step d).

Mother liquor which is obtained in the filtration step b) of the process of the present invention may be mixed with used washing liquors resulting from the washing step d). The mixture can be distilled in a known manner to remove water, acetone and a small part of phenol, preferably at an absolute pressure of from 150 to 750 mbar (15 to 75 kPa), more preferably from 220 to 620 mbar (22 to 62 kPa). A part of the distilled mixture of phenol/acetone/water is preferably recycled to the washing step d) of the present invention.

From the adduct of a bis(4-hydroxyaryl)alkane and a phenolic compound which has been obtained according to the process of the present invention the bis(4-hydroxyaryl)alkane can be recovered by melting the adduct and distilling off the phenolic compound. The recovered phenolic compound, such as phenol, may be recycled to a reaction mixture for producing the bis(4-hydroxyaryl)alkane or to step d) of the present invention wherein the adduct crystals are washed. The distillation is preferably carried out at a temperature of from 70° C. to 240° C., more preferably from 150° C. to 230° C. at a preferred pressure of from 2 to 600 mbar (0.2 to 60 kPa), more preferably from 5 to 160 mbar (0.5 to 16 kPa).

Bisphenol A recovered according to the process of the present invention generally has a concentration of less than 1400 ppm 2-(2-hydroxyphenyl)-2-(4-hydroxyphenyl)propane (o,p-isomer), preferably less than 1300 ppm o,p-isomer, more preferably less than 1100 ppm o,p-isomer, and most preferably less than 1000 ppm o,p-isomer. It has preferably a color of less than 10 APHA.

In the FIGURE the Reference Numbers Mean:
1: Suspension feed zone
2: Pre-drying zone
3a: first wash zone
3b: second wash zone
4: intermediate drying zone
5: drying zone
6: filtration cell
7: filter cloth
8: adduct cake
9: conduit
10: control head
11a, 11b, 11c: gas feed nozzles
12a. 12b: liquid feed nozzle
13: rotary drum
14: suspension feed conduit
15: discharge zone The present invention is further illustrated by the following examples which should not be construed to limit the scope of the present invention. Unless otherwise indicated, all parts and percentages are by weight. The content of the impurity 2-(2-hydroxyphenyl)-2-(4-hydroxyphenyl)propane (o,p-isomer) is analyzed by gas chromatography. The color of the bisphenol A is determined according to method APHA-ASTM, Test Method D 1209-84 (Reapproved 1988). A low APHA number means a bright color.

EXAMPLE 1 (COMPARATIVE, BUT NOT PRIOR ART)

A suspension comprising 14.8 percent of crystalline bisphenol A:phenol adduct, 2.7 of percent of o,p-isomer of bisphenol A, 2.6 of percent of water, 0.5 percent of acetone, 3.4 percent of other by-products and the remainder being phenol, was fed to a continuous pressure filter at a rate of 11720 kg/hour, where the pressure of the suspension is 1.4 bars. In the filtration step the adduct crystals were separated from the mother liquor. The adduct cake was washed in a first washing stage with 425 kg/hour of wash phenol and in a second washing stage with 475 kg/hour of wash phenol. The temperature of the wash phenol used for washing was 55° C. After the washing stages the cake was dried with nitrogen at a pressure of 1.9 bars to a residual moisture content of 30 percent, based on the weight of the dry adduct cake. Nitrogen was used to discharge the cake from the pressure filter. 2060 kg/hour of moist adduct crystals including 450 kg/hour of phenol as moisture were passed to a melt tank. The mixture was heated to 154° C., melted and fed to a distillation device wherein phenol was distilled off in three vacuum columns at temperatures of 164° C., 175° C. and 186° C. and at absolute pressures of 165 mbar, 75 mbar and 40 mbar. 1130 kg/hour of bisphenol A were obtained. The bisphenol A had a concentration of 1450 ppm of o,p-isomer of Bisphenol A and a color of 10 APHA.

The separated mother liquor that contains phenol, bisphenol A, by-products, unreacted acetone and formed water was fed to a distillation column to separate water and acetone from the mixture.

EXAMPLE 2

11720 kg/hour of the same suspension as in Example 1 were fed to a continuous pressure filter, where the pressure of the suspension was 1.4 bars. In the filtration step the adduct crystals were separated from the mother liquor. The adduct crystals were pre-dried with nitrogen at a pressure of 1.9 bars and a temperature of 51° C.

The adduct cake was washed in two washing stages, dried, and further processed as described in Example 1. 1130 kg/hour of bisphenol A were obtained. The bisphenol A had a concentration of 1040 ppm of o,p-isomer of Bisphenol A and a color of 8 APHA.

The separated mother liquor that, contains phenol, bisphenol A, by-products, unreacted acetone and formed water was treated as in Example 1.

EXAMPLE 3 (COMPARATIVE, BUT NOT PRIOR ART)

11720 kg/hour of the same suspension as in Example 1 were fed to a continuous pressure filter, where the pressure of the suspension was 1.4 bars. In the filtration step the adduct crystals were separated from the mother liquor.

The adduct cake was washed in a first washing stage with 425 kg/hour of a phenol/acetone/water mixture, which comprises 7.2 percent of phenol, 1.7 percent of acetone and water, at a temperature of 42° C. The washed adduct cake was subjected to an intermediate drying step with nitrogen at a pressure of 1.9 bars and a temperature of 51° C. In a second washing stage the adduct cake was washed with 475 kg/hour wash phenol. The temperature of the wash phenol was 55° C. After the second washing stage the adduct cake was dried with nitrogen at a pressure of 1.9 bars at a temperature of 55° C. to a residual moisture content of 30 percent, based on the weight of the dry adduct cake. Nitrogen was used to discharge the cake from the pressure filter.

2060 kg/hour of moist adduct crystals including 450 kg/hour of phenol as moisture were passed to a melt tank. 1130 kg/hour of Bisphenol A were obtained. The Bisphenol A had a concentration of 1240 ppm of o,p-isomer of bisphenol A and a color of 7 APHA.

The separated mother liquor that contains phenol, Bisphenol A, by-products, non-reacted acetone and formed water was treated as in Example 1.

EXAMPLE 4

11720 kg/hour of the same suspension as in Example 1 were fed to a continuous pressure filter, where the pressure of the suspension was 1.4 bars. In the filtration step the adduct crystals were separated from the mother liquor. The adduct crystals were pre-dried with nitrogen at a pressure of 1.9 bars and a temperature of 51° C.

The adduct cake was washed in two washing-stages, dried, and further processed as described in Example 3. 1130 kg/hour of bisphenol A were obtained. The bisphenol A had a concentration of 710 ppm of o,p-isomer of bisphenol A and a color of 2 APHA.

The separated mother liquor that contains phenol, bisphenol A, by-products, unreacted acetone and formed water was treated as in Example 1.

What is claimed is:

1. A process for recovering a solid adduct of a bis(4-hydroxyaryl) alkane and a phenolic compound from a suspension comprising the adduct, wherein the process comprises the steps of
   a) supplying the suspension to a rotary pressure filter,
   b) filtering the supplied suspension in the rotary pressure filter to retain adduct as an adduct cake,
   c) pre-drying the adduct cake with an inert gas at a pressure of from 0.2 to 6 bar above atmospheric, d) washing the pre-dried adduct cake,
e) drying of the washed adduct cake, and
f) discharging the washed, dried adduct cake from the rotary filter.

2. The process of claim 1 wherein the process is carried out in a phenol-tight and and gas-tight rotary pressure filter for continuous operation.

3. The process of claim 1 wherein the rotary pressure filter comprises several filtration cells.

4. The process of claim 1 wherein the rotary pressure filter comprises a rotary drum comprising a suspension feed zone, a pre-drying zone, a first wash zone, an intermediate drying zone, a second wash zone, a drying zone, and a discharge zone.

5. The process of claim 1 wherein the suspension is fed into the rotary pressure filter by means of static descending force.

6. The process of claim 1 wherein the adduct cake is pre-dried with nitrogen at a pressure of from 0.6 to 3.8 bar above atmospheric.

7. The process of claim 1 wherein the pre-dried adduct cake is first washed with a mixture of phenol, acetone and water and then with phenol.

8. The process of claim 1 wherein the pre-dried adduct cake is washed with phenol.

9. The process of claim 1 wherein in step d) the pre-dried adduct cake is washed in two stages with an intermediate drying step,
in step e) the washed adduct cake is dried, and
in step f) the washed and dried adduct cake is discharged from the rotary pressure filter.

10. The process of claim 1 wherein the suspension comprising the adduct results from the reaction of a stoichiometric excess of a phenolic compound with a carbonyl compound in the presence of an acidic cation exchange resin as a catalyst and treatment of the resulting product mixture in a crystallization device.

11. The process of claim 1 wherein an adduct of bisphenol-A and phenol is recovered.

12. A process for recovering a bis(4-hydroxyaryl)alkane wherein the adduct recovered according to the process of claim 1 is melted and the phenolic compound is distilled off.

13. The process of claim 2 wherein the rotary pressure filter comprises several filtration cells.

14. The process of claim 13 wherein the rotary pressure filter comprises a rotary drum comprising a suspension feed zone, a pre-drying zone, a first wash zone, an intermediate drying zone, a second wash zone, a drying zone, and a discharge zone.

15. The process of claim 14 wherein the adduct cake is pre-dried with nitrogen at a pressure of from 0.6 to 3.8 bar above atmospheric.

16. The process of claim 15 wherein the pre-dried adduct cake is first washed with a mixture of phenol, acetone and water and then with phenol.

17. The process of claim 15 wherein the pre-dried adduct cake is washed with phenol.

18. The process of claim 15 wherein
in step d) the pre-dried adduct cake is washed in two stages with an intermediate drying step,
in step e) the washed adduct cake is dried, and
in step f) the washed and dried adduct cake is discharged from the rotary pressure filter.

19. The process of claim 15 wherein the suspension comprising the adduct results from the reaction of a stoichiometric excess of a phenolic compound with a carbonyl compound in the presence of an acidic cation exchange resin as a catalyst and treatment of the resulting product mixture in a crystallization device.

20. The process of claim 15 wherein an adduct of bisphenol-A and phenol is recovered.

* * * * *